(12) United States Patent
Traugh et al.

(10) Patent No.: US 6,228,989 B1
(45) Date of Patent: May 8, 2001

(54) PEPTIDE SUBSTRATES PHOSPHORYLATED BY P21-ACTIVATED PROTEIN KINASE

(75) Inventors: Jolinda A. Traugh; Polygena T. Tuazon, both of Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/190,964

(22) Filed: Nov. 13, 1998

(51) Int. Cl.$^7$ ....................................................... C07K 1/00
(52) U.S. Cl. .......................... 530/350; 435/23; 435/226; 435/320.1; 435/69.1; 530/328; 530/329; 530/350; 530/380
(58) Field of Search ........................ 435/23, 226, 320.1, 435/69.1; 530/328, 329, 350, 380

(56) References Cited

FOREIGN PATENT DOCUMENTS

WO 9727865 A1 * 8/1997 (WO) .

OTHER PUBLICATIONS

Kennelly et al., Consensus Sequences as Substrate Specificity Determinants for Protein Kinases and Protein Phosphatases, J. Biol. Chem., 266(24):15555–15558 (1991).*
Tuazon et al., Determinants for Substrate Phosphorylation by p21–Activated Protein Kinase, Biochemistry, 36(51): 16059–16064 (1997).*
Tuazon, P.T., et al., J. Biol. Chem., 259, 541–546 (1984).
Leis, J., et al., J. Biol. Chem., 259: 7726–7732 (1984).
Fu, X., et al., J. Biol. Chem., 260: 99411–99470 (1985).
Fu, X., et al., J. Biol. Chem., 263: 2134–2139 (1988).
Walter, B.N., et al., J. Biol. Chem., 273: 28733–28739 (1998).
Tuazon, P. T., et al., Determinants for Substrate . . . Biochemistry, vol. 36, No. 51: 16059–16064 (1997).
Tuazon, P. T., et al., Autophosphorylation and Protein Kinase . . . Biochemistry, Vo.. 37, No. 48: 17024–17029 (1998).
Yu, J–S., et al., Identification of the regulatory . . . Biochem., J., 334, 121–131 (1998).
Yang, S–D., et al., J. Biol. Chem., vol. 269, No. 47, Issue of Nov. 25: 29855–29859 (1994).
Ding, Jl, et al., J. Biol. Chem., vol. 268, No. 23, Issue of Aug. 15: 17326–17333 (1993).
Ding, J., et al., J. Biol. Chem., vol. 271, No. 40, Issue of Oct. 4: 24869–24873 (1996).
Bokoch, G., et al., J. Biol. Chem., vol. 273, No. 14, Issue of Apr. 3: 8137–8144 (1998).

* cited by examiner

Primary Examiner—Christopher S. F. Low
Assistant Examiner—Stephen Tu
(74) Attorney, Agent, or Firm—Fulbright & Jaworski L.L.P.

(57) ABSTRACT

The determinants for phosphorylation of substrates by γ-PAK have been identified by examining the kinetics of phosphorylation of a series of synthetic peptides. The recognition sequence for γ-PAK contains two basic amino acids in the −2 and −3 positions, as represented by (K/R)RXS, in which the −2 position is an arginine, the −3 position is an arginine or a lysine, and X can be an acidic, basic, or neutral amino acid. A basic amino acid in the −1 or −4 position improves the rate of phosphorylation. Alternatively, an acidic amino acid in the −1 position increases the rate (2.5-fold), as does an acidic residue in the −4 position, although to a lower extent (1.6-fold). Proline in the −1 or +1 position has a deleterious effect and inhibits phosphorylation by γ-PAK. The substrate requirements of other protein kinases, such as cAMP-dependent protein kinase (PKA) and $Ca^{2+}$/phospholipid-dependent protein kinase (PKC), have been compared with γ-PAK using the same peptides. An acidic residue in the −1 position negatively affects PKA and PKC; thus, peptides containing the sequence KRES can be used in assays for γ-PAK activity.

5 Claims, No Drawings

PEPTIDE SUBSTRATES PHOSPHORYLATED BY P21-ACTIVATED PROTEIN KINASE

STATEMENT REGARDING FEDERALLY SPONSORED RESEARCH OR DEVELOPMENT

This invention was made with Government support under Grant No. GM26738, awarded by the National Institutes of Health. The Government has certain rights in this invention.

TECHNICAL FIELD OF THE INVENTION

The present invention involves peptides and their use in assays for protein kinase activity.

BACKGROUND OF THE INVENTION

γ-PAK (also known as PAK2), a member of the p2I-activated protein kinase (PAK) family [Lim, L., et al., *Eur. J. Biochem.*, 242:171–185 (1996); Sells, M. A., *Trends Cell Biol.*, 7: 180–167 (1997); and Jakobi, R., et al., *J. Biol. Chem.*,271:6206–6211 (1996) ] and formerly designated PAK I, is a serine/threonine kinase of 58 000 Da found in a number of tissues and species [Tahara, S. M., et al., *J. Biol. Chem.*, 256:11558–11564 (1981); Tahara, S. M., et al., *Eur. J. Biochem.*, 126:395–399 (1982); Tuazon, P. T., et al., *Eur. J. Biochem.*, 129:205–209 (1982); Tuazon, P. T., et al., *J. Biol. Chem.*, 259,541–546 (1984); Rooney, R. D., et al., *FASEB J.*, 6:1852 (Abstract) (1992); Rooney, R. D., et al., *J. Biol. Chem.*, 271:21498–21504 (1996) and Benner, G. E., et al., *J. Biol. Chem.*, 270:21121–21128 (1995)]. γ-PAK was first identified in rabbit reticulocytes as an inactive holoenzyme that could be activated in vitro by limited proteolysis with trypsin, chymotrypsin, or a $Ca^{2+}$-stimulated protease, hence the initial nomenclature of protease-activated kinase (PAK) I [Tahara, S. M., et al., (1981), supra and Tahara, S. M., et al., (1982), supra]. Limited proteolysis of the inactive holoenzyme with trypsin produces a catalytically active peptide of 37 000 Da that contains the catalytic domain and a part of the regulatory domain [Jakobi, R., et al., supra]. The enzyme from rabbit reticulocytes has been shown to be highly homologous to γ-PAK from human [Manser, E., et al., *Nature*, 367:40–46 (1994)] and rat [Martin, G. A., et al., *EMBO J.*, 14:1970–1978 (1995) with some homology to STE 20 from yeast [Ramer, S. W., et al., *Proc. Natl. Acad. Sci. U.S.A.*, 90:452–456 (1993)]. Like other PAK enzymes [Lim, L., et al., supra and Sells, M. A., supra], γ-PAK can bind small G proteins such as Cdc42 and Rac in the presence of GTP to stimulate autophosphorylation, resulting in activation of the protein kinase activity.

γ-PAK is also proteolytically activated in vivo during early apoptosis, and in vitro, by Caspase 3 (CCPP32) [Rudel, T., et al., *Science*, 276:1571–1574 (1997); Lee, N., et al., *Proc. Natl. Acad, Sci U.S.A.*, 94:13642–13647 (1997); and Walter, B. N., et al., *J. Biol. Chem.*, 273:28733–28739 (1998)]. Cleavage produces a regulatory domain of 27,000 Da and an active catalytic domain of 34,000 Da [Walter, B. N., et al., supra].

γ-PAK activity is elevated in serum-starved and quiescent cells and is drastically reduced in actively dividing cells. In frog eggs, γ-PAK activity and protein are high in frog oocytes and are reduced following fertilization and at the 2-cell stage. In the 4- and 16–32-cell stages, γ-PAK reappears, but mainly as the inactive form [Rooney, R. D., et al., (1996), supra]. Injection of γ-PAK into one blastomere of 2-cell frog embryos results in cleavage arrest, while the noninjected blastomere continues to divide through mid- to late-cleavage. These observations suggest that γ-PAK is involved in the maintenance of cells in a nondividing state [Rooney, R. D., et al, (1996), supra].

γ-PAK has been shown to phosphorylate a number of protein substrates such as histones 2B and 4 [Tahara, S. M., et al., (1981), supra]; myosin light chain from smooth and skeletal muscle [Tuazon, P. T., et al., (1982), supra and Tuazon, P. T., et al, (1984), supra]; translation initiation factors elF-3, elF-4B, and elF-4F [Tahara, S. M., et al., (1982), supra and Tuazon, P. T., et al., *J. Biol Chem.*, 264:2773–2777 (1989)]; and avian and Rous sarcoma virus nuclear capsid protein NC [Leis, J., et al., *J. Biol. Chem.*, 259:7726–7732 (1984); Fu, X., et al., *J. Biol. Chem.*, 260:99411–9947) (1985); and Fu, X., et al., *J. Biol. Chem.*, 263:2134–2139 (1988)]. Phosphorylation of myosin light chain in smooth muscle by γ-PAK increases the actin-activated myosin ATPase activity to the same extent as that observed upon phosphorylation by the $Ca^{2+}$ calmodulin-dependent myosin light chain kinase [Tuazon, P. T., et al., (1984), supra]. In the Rous sarcoma virus nucleocapsid protein NC, phosphorylation by γ-PAK at serine 40 increases the affinity for single-strand RNA by up to 100-fold [Fu, X., et al., (1985, supra]. Studies with site-specific mutants of NC indicate phosphorylation by γ-PAK can regulate binding to viral RNA [Fu, X., et al., (1988), supra]. Thus, it appears from the diversity of substrates that γ-PAK may be involved in regulation of multiple pathways of cell metabolism.

One approach to elucidate the role of protein kinases in general, and γ-PAK in particular, is to identify their substrates. The search for possible substrates can be facilitated by a knowledge of the amino acids critical for efficient phosphorylation. It is generally accepted that the primary sequence around the phosphorylation site plays a crucial role in the recognition of substrates for a number of protein kinases [Kennelly, P. J., et al., *J. Biol. Chem.*, 266:15555–15558 (1991)]. In these studies, determinants for phosphorylation by γ-PAK have been characterized using synthetic peptides patterned after the phosphorylation site identified as Ser 40 in the sequence PKKRKSGL in the Rous Sarcoma virus nuclear capsid protein NC, which is similar to γ-PAK sites identified in other proteins [Leis, J., et al., supra]. A model peptide KKRKSAA was synthesized and the amino acids around the phosphorylation site in the model peptide were systematically substituted with other amino acid residues to determine the minimum phosphorylation sequence for γ-PAK. The rates of phosphorylation of the peptides by γ-PAK were compared with those obtained with two other protein kinases that require basic residues around the phosphorylation site, protein kinase A (PKA) and protein kinase (PKC). On the basis of the substrate specificity requirements, a synthetic peptide that could be useful in characterizing γ-PAK in complex mixtures of protein kinases, such as crude extracts of cells or tissues, has been identified.

SUMMARY OF THE INVENTION

The present invention satisfies the need for a substrate that can be used to detect and differentiate γ-PAK from other protein kinases present in a sample. A peptide that is a selective substrate for PAK is provided, having the amino acid sequence:

$$X_1X_2X_3R_4X_5X_6X_7X_8 \qquad (1)$$

wherein $X_1$ and $X_8$ together equal 0 to 4 amino acids, each of which is independently selected; $X_2$, $X_5$ or both $X_2$ and $X_5$ is an acidic amino acid; $X_3$ is arginine or lysine; $R_4$ is arginine; $X_5$ and $X_7$ are not proline; and $X_6$ is serine or threonine. Preferably, at least one of $X_2$ and $X_5$ is selected from the group consisting of aspartic acid, glutamic acid, phosphoserine, and phosphothreonine. The most preferred peptide substrates which are highly specific substrates for PAK are AKRESAA (SEQ ID NO:1) and EKRASAA (SEQ ID NO:2).

Another embodiment of the present invention is a peptide that is a highly efficient substrate for a protein kinase, such as PAK, which has the amino acid sequence:

$$X_1X_2X_3R_4X_5X_6X_7X_8 \qquad (2)$$

wherein $X_1$, $X_2$, $X_7$, and $X_8$ together equal 1 to 6 amino acids, each of which is independently selected; at least one of $X_2$ and $X_5$ is an acidic or basic amino acid; $X_3$ is arginine or lysine; $R_4$ is arginine; $X_5$ is an independently selected amino acid; and $X_6$ is serine or threonine.

The peptide substrates of the present invention include preferred embodiments, such as AKRKSAA (SEQ ID NO:3), KKRASAA (SEQ ID NO:4), ARRASM (SEQ ID NO:5), AKRASM (SEQ ID NO:6), PKRASM (SEQ ID NO:7), KKRKSAA (SEQ ID NO:8), KKRKSGL (SEQ ID NO:9), YNKRSTTI (SEQ ID NO:10), GVKRISGL (SEQ ID NO:11), APKRGSGK (SEQ ID NO:12), and CLRRDSHK (SEQ ID NO:13).

The peptide substrates of the present invention can be used in an assay for PAK activity. The steps of the assay include: first providing a reaction mixture comprising the peptide of formula (1) or (2), ATP, magnesium and a sample, wherein the sample is believed to contain PAK; then allowing the reaction to continue so that the peptide is phosphorylated by any PAK present in the sample; and finally detecting the phosphorylated peptide to determine the presence of any PAK in the sample. The PAK activity detected can be that of α-, β-, or γ-PAK.

The sample can be pretreated with Cdc42(GTPγS) or Rac(GTPγS) or by caspase 3 (also known as CPP32) prior to assay to activate inactive forms of PAK.

Moreover, the assay may be compared to the results obtained with another protein kinase, such as protein kinase C (PKC) or protein kinase A (PKA).

The assay uses a reaction mixture which includes the peptide substrate, ATP, and divalent magnesium. Accordingly, mixtures and kits are provided for use in the assay, which includes components needed to conduct the reaction.

The assay of the present invention can be advantageously used in conjunction with a method of purifying γ-PAK. The purification method includes the steps of; preparing a cell extract; separating the cell extract into fractions; and testing the fractions for γ-PAK activity using the assay of claim 6.

These and other features of the invention will become better understood with reference to the following description and appended claims.

DETAILED DESCRIPTION OF THE INVENTION

The present invention includes a peptide which functions as a highly efficient and/or specific substrate for an activated protein kinase, such as the p21-activated protein kinase, γ-PAK. In the presence of a phosphoryl donor, such as ATP, the peptide substrate is phosphorylated by the protein kinase. The phosphorylated peptide may be detected by a variety of techniques, such as colorimetric, fluorometric, radioactive or immunological detection or mass spectrometry, thereby ascertaining the level of protein kinase present.

For purposes of shorthand designation of the peptide substrates described herein, amino acids are identified using the single-letter alphabet of amino acids, i.e.

| Ala | A | Alanine | Leu | L | Leucine |
|---|---|---|---|---|---|
| Arg | R | Arginine | Lys | K | Lysine |
| Asn | N | Asparagine | Met | M | Methionine |
| Asp | D | Aspartic acid | Phe | F | Phenylalanine |
| Cys | C | Cysteine | Pro | P | Proline |
| Gln | Q | Glutamine | Ser | S | Serine |
| Glu | E | Glutamic acid | Thr | T | Threonine |
| Gly | G | Glycine | Trp | W | Tryptophan |
| His | H | Histidine | Tyr | Y | Tyrosine |
| Ile | I | Isoleucine | Val | V. | Valine |

Except where specified otherwise, an "X" represents any naturally occurring L-amino acid.

Preferred substrate determinants for phosphorylation by γ-PAK have been identified using a series of synthetic peptides patterned after the sequence KKRKSGL (SEQ ID NO:9), which is the site phosphorylated in the nucleocapsid protein NC in vivo and in vitro by γ-PAK [Leis, J., et al., supra]. The phosphorylation determinants have been shown in these studies to be two basic amino acids in the −2 and −3 positions (relative to the serine or threonine residue that is phosphorylated), as represented by (K/R)RXS, where X can be an acidic, basic, or neutral amino acid. However, proline was shown to be inhibitory. When lysine is in the −2 position and arginine is in the −3 position, the peptide is not phosphorylated by γ-PAK, suggesting lysine in the −2 position is detrimental for γ-PAK recognition. Peptides with only a lysine at the −3 position (AKAASAA (SEQ ID NO:14)) did not serve as substrate for γ-PAK. However, an arginine in the −2 or −3 position can serve as a minimum recognition determinant since both AARASAA (SEQ ID NO:15) and ARAASVA (SEQ ID NO:16) were phosphorylated, although at a much slower rate (40%) compared to AKRASAA (SEQ ID NO:6).

Accordingly an efficient peptide substrate for γ-PAK is defined by the following formula:

$$X_1X_2X_3R_4X_5X_6X_7X_8 \qquad (2)$$

wherein $X_1$, $X_2$, $X_7$, and $X_8$ together equal 1 to 6 amino acids, each of which is independently selected; at least one of $X_2$ and $X_5$ is an acidic or basic amino acid; $X_3$ is arginine or lysine; $R_4$ is arginine; $X_5$ is an independently selected amino acid; and $X_6$ is serine or threonine.

The $K_m$ of γ-PAK for synthetic peptides containing the phosphorylation sequence (K/R)RXS ranges from about 0.2–3.5 mM and the $V_{max}$ varies from about 1 to 7 pmol/min. An additional basic residue in the −4 or −1 position, such as KKRASM (SEQ ID NO:4) or AKRKSM (SEQ ID NO:3), slightly improves the $K_m$ or the $V_{max}$, resulting in higher $V_{max}/K_m$ values, e.g., greater than about 4 pmol/min/mM. A fourth basic amino acid, as in KKRKSAA (SEQ ID NO:8), is no better than the peptides with three basic residues. Surprisingly, an acidic residue in the −1 or −4 position improves the rate of phosphorylation. For example, EKRASAA (SEQ ID NO:2) has a $V_{max}$ of 2.48 pmol/min and a $V_{max}/K_m$ of 2.8 pmole/min/mM. Similarly, AKRESAA (SEQ ID NO:1) has a $V_{max}$ of 6.62 pmole/min, and a $V_{max}/K_m$ of 4.9 pmol/min/mM. Accordingly, efficient peptide substrates of the present invention will generally have a $V_{max}/K_m$ value of about 1 to about 5 pmol/min/mM. Preferred peptide substrates will have $V_{max}/K_m$ values of greater than about 2 pmol/min/mM and the most preferred peptide substrates will have $V_{max/Km}$ values of greater than about 4 pmol/min/mM.

This phosphorylation sequence is similar to, but different from, those established for PKA and PKC. Lysine at −3 inhibits PKA and also PKC, although to a lesser extent, while both protein kinases can phosphorylate the peptide with lysine at −2 and arginine at −3 at a favorable rate. In contrast to γ-PAK, PKA and PKC cannot tolerate acidic residues in either the −1 or −4 position. Accordingly, a peptide substrate that is selective for γ-PAK is defined by the following formula:

$$X_1X_2X_3R_4X_5X_6X_7X_8 \tag{1}$$

wherein $X_1$ and $X_8$ together equal 0 to 4 amino acids, each of which is independently selected; $X_2$, $X_5$ or both $X_2$ and $X_5$ is an acidic amino acid; $X_3$ is arginine or lysine; $R_4$ is arginine; $X_5$ and $X_7$ are not proline; and $X_6$ is serine or threonine. The acidic amino acids selected for $X_2$ and/or $X_5$ are preferably aspartic acid or glutamic acid, but may also be modified amino acids such phosphoserine or phosphothreonine.

Phosphorylation of the peptide represented by formulas (1) and (2) above occurs at $X_6$, i.e., at the serine or threonine residue. The phosphorylated residue is preceded on the amino-terminal side by at least two basic amino acids at $X_3$ and $R_4$. Preferably, the basic amino acid at $X_3$ is arginine or lysine, whereas $R_4$ is invariably arginine.

Ideally, the number of amino acids composing the peptide substrates of the present invention are kept to a minimum, while still being of sufficient size to be recognized and serve as substrate at the active site of a protein kinase. It will be appreciated that as the number of of amino acid residues comprising the peptide substrate of the present invention is increased, the production of the peptide, such as by chemical synthesis, is rendered substantially more difficult, time-consuming, and expensive. To this end, the number of amino acid residues represented by the designations $X_1$, $X_2$, $X_7$, and $X_8$ in formulas (1) and (2) above is generally about 1 to 6 amino acids, preferably 2 to 4 amino acids and most preferably about 3 amino acids. The number of residues represented $X_1$ and $X_8$ of formula (1), which is selective for PAK is preferably about 0 to 4 amino acids, most preferably about 1 amino acid.

Preferred versions of the peptide substrate of the present invention specify additional amino acid residues, $X_2$, $X_5$, and $X_7$ that can contribute to the specificity and/or efficiency of the peptide substrate. For example, preferred peptide substrates containing acidic amino acids in the −1 ($X_5$) or −4 ($X_7$) position, such as AKRESAA (SEQ ID NO:1) or EKRASAA (SEQ ID NO:2), can be used to assay specifically for γ-PAK in crude extracts of cells or tissues. It is unlikely that calmodulin-dependent protein kinases and p90 rsk, which also recognize basic amino acids, will phosphorylate the above peptides. A survey of known protein substrates for calmodulin-dependent protein kinases and insulin-stimulated protein kinase 1 (ISPK-1), the mammalian homologue of p90 rsk, shows that they contain arginine in the −3 position; no substrates containing lysine in the −3 position or acidic residues in the −1 or −4 position have been identified [Songyang, Z., et al., *Mol. Cell. Biol.*, 16:6486–6493 (1996) and Donella-Deana, A., et al, *Biochim. Biophys. Acta*, 1178:189–193 (1993)].

Proline in the −1 or +1 position has a deleterious effect on γ-PAK recognition. Accordingly, preferred versions of the peptide substrate will not have a proline residue at $X_5$ or $X_7$. The detrimental effect of proline is interesting since proline in the −1 or +1 position is critical for substrate phosphorylation by the proline-directed protein kinases, such as mitogen-activated protein kinase (MAPK) and cell division control 2 kinase (cdc2), which are involved in signal transduction pathways that stimulate cell growth. Since γ-PAK has been shown to have cytostatic properties and appears to be involved in maintaining cells in a nondividing state [Rooney, R. D., et al., (1992), supra and Rooney, R. D., et al., (1996), supra], the hypothesis that sites phosphorylated by γ-PAK cannot be phosphorylated by the proline-directed protein kinases and vice versa is consistent with these observations.

Identification of potential substrates for γ-PAK is facilitated by a knowledge of the recognition/phosphorylation requirements. As shown in Table 6 (see also, Example 5 below), the phosphorylation sequence, (K/R)RXS, is found in substrates phosphorylated by γ-PAK, such as the Rous sarcoma virus nucleocapsid protein NC, histone 4, histone 2B, myelin basic protein, and prolactin. Proteins that are not substrates for γ-PAK, such as casein, histone 1, cdc42, and rac1 (data not shown), do not contain a potential phosphorylation site. Protamine contains RRXS as a possible phosphorylation site, but it is not a good substrate for γ-PAK. It is possible that the unique structure of protamine resulting from an abundance of arginine residues may block the predicted phosphorylation site from phosphorylation by γ-PAK and that secondary/tertiary structure may exert some influence on substrate specificity. Accordingly, preferred peptide substrates for γ-PAK include the amino acid sequences KKRKSGL (SEQ ID NO:9), YNKRSTTI (SEQ ID NO:10), GVKRISGL (SEQ ID NO:11), and APKRGSGK (SEQ ID NO:12), which are derived from the phosphorylation sequences of Rous sarcoma virus nucleocapsid protein NC, histone 2B, histone 4, and myelin basic protein, respectively.

As discussed above, the serine or threonine residue of the peptide substrate of the present invention is PHOSPHORYLATED by a protein kinase (PK) in accordance with the following equation:

$$\text{Peptide} + \text{ATP} \xrightarrow{\text{PK}} \text{Peptide-Phosphate} + \text{ADP} \tag{3}$$

Also, as previously described, the protein kinase employed in formula (3) above is most preferably PAK. The PAK used in the assay of the present invention can be activated by the small p21 G proteins, Cdc42 and Rac bound to GTPγS or by proteolysis, followed by autophosphorylation as described in patent application Ser. No. 08/615,942 and Walter, B. N., et al., supra, which are incorporated herein in their entirety. As described more fully in the examples below, the phosphorylated peptide provides a straightforward and accurate technique for assaying for the precursor of PAK.

The peptide substrate of the present invention as defined in formulas (1), (2), and (3) above can be produced by several different methods, such as by recombinant DNA methods or chemical synthesis.

Preferably, the peptide of the present invention is synthesized by the solid phase technique developed by R B Merrifield, which permits the peptide to be built residue by residue from the carboxyl terminal amino acid to the amino terminal amino acid either manually or with an automated commercially available synthesizer. Details of the solid phase technique are well known, such as those set forth in the experimental methods of the examples described below.

If recombinant DNA methods are used, a synthetic oligonucleotide encoding the amino acid sequence of the peptide can be produced by well-known techniques. The synthetic oligonucleotide can then be inserted within a cloning vector, such as a plasmid or bacteriophage, which in turn may be employed to transform a compatible prokaryotic or eukaryotic host for replication of the vector and expression of the peptide, alone or as a fusion product.

For use with the peptide substrate of the present invention, γ-PAK can be prepared by standard techniques, such as described by [Jakobi, R., et al., supra; Tahara, S. M., et al., (1981), supra; and Rooney, R. D., et al., (1996), supra] which are incorporated herein by reference. PAK is ubiquitous and can be purified from a variety of eukaryotic cells, e.g., rabbit reticulocytes. Moreover, PAK can be cloned and expressed, e.g., as a GST-fusion protein in insect cells. Fractions are collected and assayed as generally described below and as detailed in the experimental methods described below. The assayed fractions found to contain γ-PAK activity are pooled and further concentrated.

The peptide substrate of the present invention may be employed to assay for the presence of γ-PAK, for instance, during the above outlined process of preparing the enzyme. The assay is based on the phosphorylation of the peptide substrate by γ-PAK. In the assay, the sample to be tested is mixed together with the peptide substrate, radiolabeled ATP, in the presence of divalent magnesium at approximately physiological pH. The mixture is incubated for only a brief period, e.g., for about 15–30 min at 30° C., to insure linearity of the reaction. The phosphorylated peptide is then separated from the mixture by an appropriate method, such as fractionation by thin layer electrophoresis or selective adsorption on P81 phosphocellulose paper as described in further detail in the examples below. The phosphorylated peptide can then be localized, for example by autoradiography, and the level of radioactivity determined, for example, by liquid scintillation spectrophotometry. The level of radioactivity is indicative of the extent to which the substrate has been phosphorylated, which in turn is indicative of the amount of γ-PAK present in the sample being assayed.

Alternatively, those of skill in the art will appreciate that there are a variety of non-radioactive methods for detecting phosphorylation of the peptide substrate. For example, a fluorescent tag can be added to peptide substrate of the present invention. The acidic changes added to the peptide upon phosphorylation cause the peptide to migrate differently from the non-phosphorylated peptide in a variety of electrophoresis systems. See,e.g., Dawson et al. ["A capillary electrophoresis-based assay for protein kinases and protein phosphatases using peptide substrates", *Analytical Biochemistry*, 220:340–3450 (1994)], which used capillary zone electrophoresis methodology. The phosphorylated and nonphosphorylated peptides are readily separated by charge using agarose-gel electrophoresis and can be identified and quantified by uv detection. [Lutz, M. P. et al., "A nonradioactive fluorescent gel-shift assay for the analysis of protein phosphatase and kinase activities toward protein-specific peptide substrates", *Analytical Biochemistry*, 220:268–274 (1994)].

Others use matrix-assisted laser desorption ionization time-of flight mass spectrometry (MALDI-TOF) to quantify the phosphopeptide. [Matsumoto, H., et al., "Nonradioactive phopshopeptide assay by matrix-assisted laser desorption ionization time-of-flight mass spectrometry", *Analytical Biochemistry*, 260:188–194 (1998)].

Antibodies specific for phosphopeptides (as compared to peptides) are available from commercial suppliers, such as New England BioLabs, Beverly, Mass. and CALBIOCHEM, La Jolla, Calif. After phosphorylation, the phosphopeptides can be detected by an ELISA method, or separated on gels and quantified by immunoblotting (Western blotting).

Accordingly, the presence of γ-PAK may be conveniently and rapidly detected and quantified by a number of assays utilizing the peptide substrates of the present invention.

EXAMPLES

Experimental Procedures

A. Materials.

γ-PAK was purified from rabbit reticulocytes to apparent homogeneity by chromatography on DEAE-cellulose, SP-Sepharose, protamine agarose, and FPLC on Mono S and Mono Q. Histone I (type IIIS), mixed histone (type IIAS), trypsin (L-1-tosylamido-2-phenylethyl chloromethyl ketone treated), soybean trypsin inhibitor, bovine serum albumin (fatty acid free), and myelin basic protein were purchased from Sigma. Purified histones 2B and 4 were purchased from Boehringer-Mannheim. Myosin light chain from rabbit skeletal muscle was a gift from Dr. James Stull, University of Texas Southwestern Medical Center, Dallas, Tex.; rat prolactin was provided by Dr. Ameae Walker, University of California, Riverside, Calif.; and the purified catalytic subunit of cAMP-dependent protein kinase from bovine heart was a gift from Dr. William H. Fletcher, J. L. Pettis Memorial V. A. Hospital, Loma Linda, Calif. Protein kinase C was purified from bovine brain according to the procedure of Walton et al. [Walton, G. M., et al., *Anal. Biochem.*, 161:425–437 (1987)], with modifications [Venema, R. C., et al., *J. Biol. Chem.*, 266:5298–5302 (1991)]. The clone for GST-Cdc42 was generously provided by Dr. Channing Der, University of North Carolina, Chapel Hill, N.C. Cellulose thin-layer chromatography sheets were from Kodak.

The 9-fluorenylmethoxycarbonyl (Fmoc)-protected amino acids, 1-hydroxy-7-azabenzotriazole (HOAt), and Fmoc-PAL-PEG-PS [[5-(4'-Fmoc-aminomethyl-3',5'-dimethoxy-phenoxy) valeric acid]-poly(ethylene glycol)-polystyrene resin] were purchased from Millipore Corp. Acetonitrile (HPLC grade), methanol (HPLC grade), glacial acetic acid, N,N-dimethylformamide (DMF), and anhydrous ethyl ether were obtained from Fisher Scientific. Liquified phenol was supplied by Mallinckrodt. Triisopropylsilane, piperidine, 1 ,3-diisopropylcarbodiimide (Dl PCDI), and redistilled trifluoroacetic acid (TFA) were purchased from Aldrich Chemical Co.

B. Peptide Synthesis.

Peptides were synthesized with an amide C-terminal group using a Millipore Model 9050 Plus peptide synthesizer using Fmoc solid phase peptide synthesis chemistries [Fields, G. B., et al., *Int. J. Pept. Protein Res.*, 35:161–214 (1990)]. A theoretical yield of ≈0.08 mmol of each peptide was synthesized on a PAL-PEG-PS resin using 4-fold excesses of the appropriate Fmoc-labeled amino acids and the HOAt/DIPCDI activating reagents. All amino acid coupling reactions were allowed to proceed for 60 min in DMF. A mixture of 20% (v/v) piperidine in DMF was used to remove Fmoc protecting groups during synthesis.

To cleave the peptide from the resin and remove side-chain protecting groups, ≈0.25 g of peptide containing resin (0.04 mmol of peptide) was placed in a vial with 3.0 mL of 88% (v/v) TFA, 5% phenol, 2% triisopropylsilane, and 5% water [Sole, N. A., et al., *J. Org. Chem.*, 57:5399–5403 (1992)]. This mixture was gently agitated for 3–3.5 h, and the mixture was poured into a sintered glass funnel to separate the liquid containing the peptide from the resin. The resin was washed with 2–3 mL of TFA; the wash was combined with the cleavage liquid and rotoevaporated to remove the majority of the TFA. The remaining liquid was injected into ice-chilled ethyl ether to precipitate the peptide. The crude precipitated peptide was washed several times with cold ether and dried under vacuum.

C. Peitide Purification and Characterization.

Crude peptide was dissolved in water to make solutions with a nominal peptide concentration between 10 and 20 mg/mL. The desired peptide product was isolated by reversed phase HPLC (Model 2700 pump, Bio-Rad Laboratories) using a 10 by 250 mm $C_{18}$ column with a 50 mm guard column (Rainin Instrument Co.). The peptide was eluted under isocratic conditions with a water-acetonitrile mobile phase containing 0.1 % TFA and ≈5% acetonitrile. The desired peptide fractions were collected, pooled, and lyophilized.

The purity of the isolated peptide was established on the basis of peak areas as determined by capillary zone electrophoresis. All separations were performed with a BioFocus 3000 CE system (Bio-Rad Laboratories) in a 50 cm length of 50 µm i.d., 360µm o.d., fused silica capillary (Polymicro Technologies Inc.) with 46.4 cm from inlet to the detector. The peptide sample was prepared by dissolving lyophilized peptide in 10 mM sodium phosphate, pH 2.5, to provide a solution with a nominal peptide concentration of 1.0 mg/mL. This solution was introduced into the capillary containing 100 mM sodium phosphate, pH 2.5, with a 1.0 psi s pressure pulse. A 200 V $cm^{-1}$ electric field was used to drive the separation, and the analytical signal was monitored with an on-column absorbance detector at 200 nm. Integration of the resulting electropherograms using Biofocus Integration Software version 5.0 (Bio-Rad Laboratories) provided relative peak areas. All peptides displayed >98% purity on this basis.

A portion of the peptide solution was diluted 20-fold with a solution of methanol/water/acetic acid (50:50:3) and analyzed by electrospray ionization-mass spectrometry (Vestec Model 201). This technique was used to establish that the mass of the collected peptide corresponded within experimental error to the calculated value for the desired peptide.

D. Phosrhorvlation Assays.

Phosphorylation of protein substrates was carried out in 35 µL reaction mixtures containing 20 mM Tris-HCl, pH 7.4, 10 mM $MgCl_2$, 30 mM 2-mercaptoethanol, 0.2 mM ATP (specific activity=1000 cpm/pmol), 2 µg of protein substrate, and 20 units of active γ-PAK (an enzyme unit is defined as the amount of enzyme that incorporates 1 pmol of phosphate into histone IIAS/ min at 30°. Under these conditions, phosphate incorporation was linear and initial rates of phosphorylation were measured. After incubation at 30° C. for 15 min, reactions were terminated by the addition of 5 µL of 100 mM nonlabeled ATP and sample buffer for gel electrophoresis [Hathaway, G. M., et al., *Methods Enzymol.*, 60:495–511 (1979)]. Reaction mixtures were subjected to SDS-PAGE on 15% polyacrylamide gels followed by autoradiography. Phosphorylation was quantified by excising the protein band and counting the incorporated $^{32}p$ in a liquid scintillation counter. The specific activity of γ-PAK was 400 pmol $min^{-1}$ $µg^{-1}$ as reported previously using 0.2 mM ATP and 1 mg/mL mixed histone as substrate [Rooney, R. D., et al., (1996), supra].

Assays with peptides (I mM) were carried out with γ-PAK (1.6–5.6 units) in 25 µL reaction mixtures incubated for 30 min at 30° C. under conditions described above, except that 0.4 mg/mL of bovine serum albumin was added and the specific activity of ATP was 300–2000 cpm/pmol. Reactions were terminated with 5 µL of 100 mM ATP, and the amount of $^{32}p$ incorporated was quantitated by precipitation of 20 µL aliquots on P81 phosphocellulose paper with 75 mM $H_3PO_4$ as described previously [Bensen, E. S., et al., *Biochim. Biophys. Acta*, 1292:249–258 (1996)]. Peptides containing only one basic amino acid were analyzed by thin-layer electrophoresis on cellulose sheets for 2 h at 600 V with pyridine/acetic acid/water (10:100:890), pH 3.5, as solvent, as described previously [Bensen, E. S., et al., supra]. Activation of γ-PAK by autophosphorylation in the presence of Cdc42(GTPγS) was performed as previously described [Jakobi, R., et al, supra]. γ-PAK was also activated by limited digestion with trypsin as described previously [Rooney, R. D., et al., (1996), supra].

$K_m$ and $V_{max}$ values were determined from Lineweaver-Burk plots of the rate of phosphorylation at four to six different peptide concentrations and at a fixed concentration of ATP (0.2 mM). Kinetic values reported are typical of two to three independent determinations, and the standard error for all reported kinetic constants is <20%. The $K_m$ for ATP was determined to be 65–80 µM at concentrations of 1–3 mM peptide. This $K_m$ value with the peptides is lower than the $K_m$ value obtained with mixed histone as substrate [Tahara, S. M., et al., (1981), supra]. Since the concentration of ATP used in these studies was significantly greater than the $K_m$ for ATP, the reported $V_{max}$ values approximate the real $V_{max}$ values.

Reactions with PKA (10.5 units) were carried out under the same conditions as with γ-PAK except that 0.14 mM ATP was used. Reactions with PKC (3.4 units) were performed as with PKA, with the addition of 0.4 mM $CaCl_2$, phosphatidylinositol (15 µg/mL), phosphatidylserine (15 µg/ mL), and 1,2-diolein (3 µg/mL), as described [Tuazon, P. T., et a., (1989), supra]. A unit of PKA or PKC is defined as the amount of enzyme that incorporates 1 pmol of phosphate/min at 30° C. into histone IIAS or histone 1, respectively.

Example 1

Basic Amino Acids as Recognition Determinants for γ-PAK.

The phosphorylation site of the Rous and avian sarcoma virus nucleocapsid protein NC in vivo was identified as Ser 40 in the sequence PKKRKSL (SEQ ID NO:18), and was shown to be the site phosphorylated by γ-PAK in vitro [Leis, J., et al., supra]. On the basis of this phosphorylation site, which was similar to sites identified in several other proteins [Leis, J., et al., supra], the peptide KKRKSM (SEQ ID NO:8) was synthesized and tested as a substrate for γ-PAK. It proved to be an efficient substrate with $K_m$ and $V_{max}$ values of 0.61 mM and 302 pmol $min^{-1}$ $µg^{-1}$, respectively. The observed $K_m$ and $V_{max}$ values were within the range of values noted for synthetic peptide substrates with other serine/threonine protein kinases including casein kinases I and II , PKA, PKC, S6 kinases, Cdc2, p44 MAP kinase, and myosin light chain kinase [Bensen, E. S., et al., supra; Umphress, J. L., et al., *Eur. J. Biochem.*, 203:239–243 (1992); Feramisco, J. R., et al., *J. Biol. Chem.*, 255:4240–4245 (1980); Marin, O., et al., *Eur. J. Biochem.*, 160:239–244 (1986); Kuenzel, E. A., et al., *J. Biol. Chem.*, 262:9136–9140 (1987); Litchfield, D. W., eta/., *FEBS Lett.*, 261:117–120 (1990); Meggio, F., etaL., *FEBS Lett.*, 237:225–228 (1988); Kemp, B. E., et al., *J. Biol. Chem.*, 260:3355–3359 (1995); Pearson, R. B., et al., *J. Biol. Chem.*, 261:25–27 (1986); Donella-Deana, A., et al., *Biochim. Biophys. Acta*, 1178:189–193 (1993); Leader, D. P., et al., *Biochim. Biophys. Acta*, 1091:426–431 (1991); Marshak, D. R., et al., *J. Biol. Chem.*, 45:391–400 (1991); Clark-Lewis, I., et al., *J. Biol. Chem.*, 266:15180–15184 (1991); Flotow, H., et al., *J. Biol. Chem.*, 267:3074–3078 (1992); House, C., et al., *J. Biol. Chem.*, 262:772–777 (1987) and Kemp, B. E., et al., *J. Biol. Chem.*, 257:13349–13353 (1982)].

TABLE 1

Relative Rates of Phosphorylation of Synthetic Peptides by γ-PAK[a]

| peptide | proteolytically activated 32P incorporated (pmol min$^{-1}$ μg$^{-1}$) | rel rate (%) | Cdc42-activated rel rate (%) |
|---|---|---|---|
| AKRESAA | 750 | 247 | 295 |
| PKRASAA | 636 | 209 | 184 |
| KKRASAA | 586 | 193 | 181 |
| AKRKSAA | 548 | 181 | 158 |
| EKRASAA | 484 | 160 | 151 |
| AKRASAA | 426 | 141 | 189 |
| ARRASAA | 391 | 129 | 134 |
| AKRASEA | 326 | 108 | 88 |
| AKRGSAA | 381 | 126 | nd |
| AKRASGA | 324 | 107 | nd |
| KKRKSAA | 302 | 100 | 100 |
| AARASAA | 169 | 56 | 56 |
| AKRPSAA | 16 | 6 | 11 |
| ARKASAA | 16 | 6 | 9 |
| AKAASAA | 5 | 2 | 3 |
| AKRASPA | 0 | 0 | 3 |
| RKKKSAA | 0 | 0 | 3 |
| KKAASAA | 0 | 0 | 3 |
| AKKASAA | 0 | 0 | 1 |
| AAKKSAA | 0 | 0 | 0 |
| AAKRSAA | 0 | 0 | 0 |
| AAAASKR | 0 | 0 | 0 |

[a]Rates of phosphorylation of peptides (1 mM) were measured with γ-PAK (5.6 units) in 0.025 mL reaction mixtures incubated for 30 min at 30° C. $^{32}$P incorporation into peptides was determined as described under Experimental Procedures.
γ-PAK was activated by autophosphorylation in the presence of Cdc42 (GTPγS) or by proteolysis as described under Experimental Procedures.
nd, not determined.

Additional peptides based on the above sequence with amino acid substitutions on the N-terminal and C-terminal sides of serine were synthesized to define the amino acids around the phosphorylation site essential for γ-PAK. Rates of phosphorylation with γ-PAK activated by limited digestion with trypsin were measured and compared to the rate of KKRKSM (SEQ ID NO:8) (Table 1). Specific basic residues on the N-terminal side of the phosphorylated serine were shown to be essential for recognition by γ-PAK. Basic amino acids on the C-terminal side, as in AAAASKR (SEQ ID NO:19), were not involved in, γ-PAK recognition/phosphorylation. Since γ-PAK is also activated by Cdc42 (GTPγS), it was important to determine whether the phosphorylation/recognition sequence was the same using both methods of activation. As shown in Table 1, similar relative rates were obtained with the peptides when ,γ-PAK was activated by autophosphorylation in the presence of Cdc42(GTPγS). Peptides that were good substrates for γ-PAK activated by trypsin were also good substrates for γ-PAK activated by Cdc42(GTPγS). Inactive γ-PAK showed <5% of the activity of the activated forms with all peptides; thus, there was no effect of peptide on activation of the inactive enzyme.

The influence of basic residues at the N terminus on the rate of phosphorylation was evaluated further by systematically varying the amino acids around the phosphorylation site. Although the peptide KKRKSAA (SEQ ID NO:8) was a good substrate, replacement of the lysine residues in either the −1 or −4 position with alanine as in KKRASAA (SEQ ID NO:4) or AKRKSM (SEQ ID NO:3) resulted in an increase in the rate of phosphorylation to 193 and 181%, respectively. Replacement of lysine at the −1 and −4 positions simultaneously, as in AKRASM (SEQ ID NO:6), also resulted in a faster rate (141%) when compared to KKRKSM (SEQ ID NO:8), but slower than the single amino acid substitution in either the −1 or −4 position. When lysine in the −3 position of AKRASAA (SEQ ID NO:6) was replaced by alanine, the resulting peptide AARASM (SEQ ID NO:15) was phosphorylated at a significantly slower rate (40 and 56%) as compared to AKRASAA (SEQ ID NO:6) and KKRKSAA (SEQ ID NO:8), respectively. When arginine in the −2 position was replaced with alanine, as in AKAASAA (SEQ ID NO:14), the peptide could not be phosphorylated by γ-PAK, suggesting that an important part of the recognition sequence is the arginine in the −2 position. In other studies, arginine in the −3 position (ARAASVA (SEQ ID NO:16)) phosphorylated at a slower rate (40%) compared to ARRASVA (SEQ ID NO:17) (100%).

TABLE 2

Kinetic Parameters for Phosphorylation of Synthetic Peptides by γ-PAK: Influence of Basic Amino Acids[a]

| peptide | $K_m$ (mM) | $V_{max}$ (pmol/min) | $V_{max}/K_m$ (pmol min$^{-1}$ mM$^{-1}$) |
|---|---|---|---|
| AKRKSAA | 0.48 | 2.34 | 4.8 |
| KKRASAA | 0.37 | 1.59 | 4.3 |
| ARRASAA | 0.65 | 2.11 | 3.2 |
| KKRKSAA | 0.61 | 1.84 | 3.0 |
| AKRASAA | 0.46 | 1.04 | 2.2 |
| AARASAA | 1.88 | 2.27 | 1.2 |
| ARKASAA | >5 | nd | nd |
| AKAASAA | >5 | nd | nd |

[a]$V_{max}$ and $K_m$ values were calculated from double-reciprocal plots of the initial rates and peptide concentrations. Rates of phosphorylation were determined using γ-PAK (1.6 units) and various concentrations of peptide (0–1.0 mM).
nd, not detected.

The importance of the type of basic residue in the −2 and −3 positions was examined further. ARRASM (SEQ ID NO:5) was as good a substrate as AKRASAA (SEQ ID NO:6), suggesting that the −3 position can be either a lysine or an arginine when arginine is in the −2 position. However, RKKKSM (SEQ ID NO:20), AKKASAA (SEQ ID NO:21), MKKSM (SEQ ID NO:22), MKRSAA (SEQ ID NO:23) and ARKASM (SEQ ID NO:24) were poor substrates, suggesting that lysine in the −2 position was not tolerated by γ-PAK even though the −3 (or−1) position was occupied by a basic amino acid. Since AARASM (SEQ ID NO:15) and ARAASVA (SEQ ID NO:16) reacted to a small but significant extent, whereas AKAASAA (SEQID NO:14) and KKAASAA (SEQ ID NO:25) did not, arginine in the −2 or −3 position, but not lysine in the −3 position, may be a minimum recognition determinant for γ-PAK. However, two basic residues in the −2 and −3 positions, with an absolute requirement for arginine in the −2 position, are more efficient for phosphorylation and more specific for recognition by γ-PAK.

To analyze further the variations in phosphorylation rates, kinetic constants for peptides with basic residues on the N-terminal side were measured as shown in Table 2. Peptides containing the sequence X(K/R)RXSM, with X as alanine or a basic amino acid, varied only slightly in the measured $K_m$ and $V_{max}$ values. The $K_m$ values (0.37–0.65 mM) were within the range observed with other protein kinases for synthetic peptides [Bensen, E. S., et al, supra; Umphress, J. L., et al., supra; Feramisco, J. R., et al., supra; Marin, O., et al., supra; Kuenzel, E. A., et al., supra,; Litchfield, D. W., et al., supra; Meggio, F., et al., supra; Kemp, B. E., et al., (1995) supra; Pearson, R. B., et al., supra; Donella-Deana, A., et al., supra; Leader, D. P., et al., supra; Marshak, D. R., et al., supra; Clark-Lewis, I., et al., supra; Flotow, H., et al., supra; House, C., et al., supra, and Kemp, B. E., et al., (1982), supra]; the $V_{max}$ values varied from 169 to 750 pmol min$^{-1}$ µg$^{-1}$. Peptides with a third basic amino acid in the −1 or −4 position had the highest overall rate as shown by the $V_{max}/K_m$ value, ~2 fold higher than that of AKRASAA (SEQ ID NO:6). Four basic amino acids on the N-terminal side, as in KKRKSAA (SEQ ID NO:8), had a reduced $V_{max}/K_m$ as compared to AKRKSM (SEQ ID NO:3) or KKRASAA (SEQ ID NO:4).

Example 2

Effects of Glutamic Acid Residue

Using AKRASAA (SEQ ID NO:6) as a model peptide, the amino acids at positions −4, −1, and +1 were varied by replacement with acidic amino acid residues, since acidic residues at these positions have been shown to inhibit recognition/phosphorylation by other protein kinases that recognize basic residues. AKRESAA (SEQ ID NO:1) had the highest rate of phosphorylation among all peptides examined (Table 1). Glutamate residues in the −1 or −4 position, as in AKRESM (SEQ ID NO:1) or EKRASAA (SEQ ID NO:2), increased the rate of phosphorylation relative to AKRASM (SEQ ID NO:6) to 175 and 113%, respectively, while a glutamate residue in the +1 position decreased the rate to 71% (Table 1). Glutamate in the −1 or +1 position increased the $K_m$ by ~3-fold, while the $K_m$ was increased by 2-fold when glutamate was in the −4 position when compared to AKRASAA (SEQ ID NO:6) (Table 3). However, $V_{max}$ values were highest with AKRESAA (SEQ ID NO:1), 6-fold higher than with AKRASAA (SEQ ID NO:6), which accounts for an increase in the overall rate ($V_{max}/K_m$) of ~2.2-fold, There was a >2-fold increase in the $V_{max}$ when glutamate was in the −4 or +1 position. Compared to AKRASAA (SEQ ID NO:6), the overall rate of phosphorylation ($V_{max}/K_m$) was 1.3-fold with glutamate in the −4 position and 0.7-fold when glutamate was in the +1 position of AKRASEA (SEQ ID NO:26).

TABLE 3

Kinetic Parameters for Phosphorylation of Synthetic Peptides by γ-PAK: Influence of Acidic Amino Acids

| peptide | $K_m$ (mM) | $V_{max}$ (pmol/min) | $V_{max}/K_m$ (pmol min$^{-1}$ mM$^{-1}$) |
|---|---|---|---|
| AKRESAA | 1.35 | 6.62 | 4.9 |
| EKRASAA | 0.89 | 2.48 | 2.8 |
| AKRASAA | 0.46 | 11.04 | 2.2 |
| AKRASEA | 1.42 | 2.22 | 1.6 |

TABLE 4

Kinetic Parameters for Phosphorylation of Synthetic Peptides by γ-PAK: Influence of Proline and Glycine[a]

| peptide | $K_m$ (mM) | $V_{max}$ (pmol/min) | $V_{max}/K_m$ (pmol min$^{-1}$ mM$^{-1}$) |
|---|---|---|---|
| PKRASAA | 0.24 | 1.10 | 4.6 |
| AKRASAA | 0.46 | 1.04 | 2.2 |
| AKRPSAA | >5 | nd | nd |
| AKRASPA | >5 | nd | nd |
| AKRGSAA | 3.52 | 6.44 | 1.8 |
| AKRASGA | 2.09 | 3.49 | 1.7 |

[a]nd, not detected.

Example 3

Effects of Proline and Glycine

Proline in the −1 or +1 position as in AKRPSAA (SEQ ID NO:27) or AKRASPA (SEQ ID NO:28) virtually abolished phosphorylation by γ-PAK (Table 1). This is not surprising because proline in these positions is a phosphorylation determinant for the proline-directed protein kinases. Proline in the −4 position, as in PKRASM (SEQ ID NO:7), decreased the $K_m$ by ≈2-fold as compared to AKRASAA (SEQ ID NO:6) but had no effect on the $V_{max}$ resulting in an overall effect of a 2-fold increase in the phosphorylation rate (Table 4).

Glycine in the −1 position, as in AKRGSM (SEQ ID NO:29), increased the $K_m$ by 7-fold over that of the peptide containing alanine at that position. At the same time the $V_{max}$ was increased by 6-fold, leading to a slight overall decrease in the phosphorylation rate. Glycine in the +1 position of AKRASGA (SEQ ID NO:30) increased the $K_m$ by 4-fold and the $V_{max}$ by 3-fold, with a slight overall decrease in rate (Table 4).

Example 4

Comparison of Rates of Phosphorylation with PKA and PKC

PKA and PKC are known to require basic amino acids on the N-terminal side of the phosphorylatable serinel threonine. To distinguish their substrate specificities from that of γ-PAK, the relative rates of phosphorylation were determined with the synthetic peptide substrates using the conditions for γ-PAK, with the addition of Ca$^{2+}$ and phospholipids for PKC. The rates shown in Table 5 are calculated with equivalent units of enzyme; the rate of phosphorylation of the peptide AKRASM (SEQ ID NO:6) is taken as 100% for all three enzymes. As would be expected, PKA preferentially phosphorylated the peptides that contained RR or RK at the −3 and −2 positions and with basic residues or proline at the −4 and −1 positions inhibitory. PKC recognized SKR>RKS>KKS. The most notable difference between γ-PAK and PKA or PKC is the effect of acidic residues on the susceptibility of the peptide to be phosphorylated. An acidic residue in the −1 or −4 position was beneficial for γ-PAK but was detrimental for both PKA and PKC (Table 5). An acidic residue in the +1 position was detrimental to PKC and PKA but only slightly reduced the rate for γ-PAK. In addition, γ-PAK could not tolerate an arginine in the −3 position when lysine was in the −2 position. On the other hand, PKC and PKA phosphorylated ARKASM (SEQ ID NO:24) much more quickly than AKRASAA (SEQ ID NO:6).

TABLE 5

Comparative Rates of Phosphorylation of synthetic Peptides by γ-PAK, PKC, and PKA[a]

| | $^{32}$P incorporated | | | | | |
|---|---|---|---|---|---|---|
| | γ-PAK | | PKC | | PKA | |
| peptide | pmol/unit | % | pmol/unit | % | pmol/unit | % |
| AKRESAA | 47.2 | 176 | 0.4 | 12 | 1.8 | 38 |
| PKRASAA | 40.5 | 151 | 8.7 | 264 | 6.9 | 144 |
| EKRASAA | 30.2 | 113 | 0.1 | 3 | 1.7 | 4 |
| AKRASAA | 26.8 | 100 | 3.0 | 100 | 4.8 | 100 |
| ARRASAA | 25.0 | 93 | 18.8 | 570 | 137.1 | 2856 |
| KKRKSAA | 19.2 | 72 | 11.1 | 370 | 19.8 | 412 |
| AKRASEA | 18.3 | 68 | 0.2 | 6 | 3.6 | 75 |
| AKRPSAA | 1.2 | 5 | 3.9 | 118 | 10.3 | 215 |
| ARKASAA | 0.9 | 3 | 5.7 | 173 | 107.5 | 2240 |
| RKKKSAA | 0.1 | 0 | 3.1 | 94 | 5.4 | 112 |
| AAAASKR | 0 | 0 | 13.3 | 403 | nd | nd |

[a]nd, not determined.

TABLE 6

Relative Rates of Phosphorylation and Phosphorylation Sequences of Proteins with γ-PAK[a]

| Substrate | $^{32}$P incorporated (pmol) | rel rate (%) | phosphorylation sequence |
|---|---|---|---|
| histone 2B | 11.0 | 100 | YNKRST$^{88}$TI |
| histone 4 | 8.3 | 74 | GVKRIS$^{47}$GL |
| myelin basic protein | 4.2 | 37 | APKRGS$^{55}$GK |
| prolactin | 1.8 | 17 | CLRRDS$^{205}$HK |
| protamine | 0 | 0 | RRRRSS$^{8}$SR |
| histone 1 | 0 | 0 | none |

[a]Sequences are for bovine histone 2B, bovine histone 4, bovine myelin basic protein, rat prolactin, protamine from salmon, and bovine histone 1. Sites phosphorylated by γ-PAK have been confirmed with histone 4.

Example 5

Substrate Specificity of γ-PAK with Proteins

A number of proteins were examined as substrates, and their relative rates of phosphorylation were compared (Table 6). Histone 4 and histone 2B had the highest rates of phosphorylation, whereas histone 1 and protamine did not serve as substrates. Relative to histone 2B, myelin basic protein and prolactin had rates of 37 and 17%, respectively.

When the phosphorylation sequences of the substrates were examined (Table 6), all of the substrates phosphorylated by γ-PAK, including histone 4, histone 2B, myelin basic protein, and prolactin, contained two basic residues in the −2 and −3 positions, with R in the −2 position in every case, as represented by (K/R)RX(S/T). Those proteins containing KRXS were phosphorylated at higher rates than those containing RRXS. The site of phosphorylation has been determined in histone 4. Protamine and histone 1 were not substrates for γ-PAK, although protamine contains a potential phosphorylation site, RRSS within the RRRRSSSR (SEQ ID NO:31) sequence.

Example 6

Analysis of Phosphorylation of Different Substrates with ATP(Mg) and ATP(Mn)

Synthetic heptapeptides were used to examine the activity of γ-PAK with manganese and magnesium. The peptides were incubated with γ-PAK (2.5 units), activated by autophosphorylation in the presence of Cdc42(GTPγS) and 10 mM MgCl$_2$ or 6 mM MnCl$_2$ as described under Experimental Procedures. AKKASAA (SEQ ID NO:21) and AKAASAA (SEQ ID NO:14) were not phosphorylated by γ-PAK using ATP(Mg) or ATP(Mn). In contrast, peptides AKRESAA (SEQ ID NO:1) were good substrates for Cdc42-activated γ-PAK. The rate of phosphorylation of the peptides with magnesium was significantly higher than with manganese, with the Mg/Mn ratios around 18. These results suggest that manganese is not a suitable cofactor for phosphorylation of exogenous substrates by γ-PAK.

Although the present invention has been described in considerable detail with reference to certain preferred versions thereof, other versions of are possible. For example, the peptide substrates of the present invention may also include a non-radioactive label. Therefore, the spirit and scope of the appended claims should not be limited to the description of the preferred versions described herein.

We claim:

1. A peptide consisting of an amino acid sequence:

$$X_1X_2X_3R_4X_5X_6X_7X_8$$

wherein $X_1$ and $X_8$ together equal 0 to 4 amino acids, each of which is independently selected;

$X_2$, $X_5$ or both $X_2$ and $X_5$ is an acidic amino acid;

$X_3$ is arginine or lysine;

$R_4$ is arginine;

$X_5$ and $X_7$ are not proline;

$X_6$ is serine or threonine, and the peptide is a selective substrate for p21-activated protein kinase (PAK).

2. The peptide of claim 1 wherein at least one of $X_2$ and $X_5$ is selected from the group consisting of aspartic acid, glutamic acid, phosphoserine, and phosphothreonine.

3. A peptide comprising an amino acid sequence selected from the group consisting of SEQ ID NO:1, SEQ ID NO:2, SEQ ID NO:6, SEQ ID NO:7 and SEQ ID NO:26, wherein said peptide is a selective substrate for p21-activated protein kinase (PAK).

4. A peptide consisting of the amino acid sequence:

$$X_1X_2X_3R_4X_5X_6X_7X_8$$

wherein $X_1$, $X_2$, $X_7$, and $X_8$ together equal 1 to 6 amino acids, each of which is independently selected;

at least one of $X_2$ and $X_5$ is an acidic or basic amino acid;

$X_3$ is arginine or lysine;

$R_4$ is arginine;

$X_5$ is an independently selected amino acid;

$X_6$ is serine or threonine; and the peptide is a substrate for p21-activated protein kinase (PAK).

5. A peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13.

\* \* \* \* \*

SEQUENCE LISTING

<160> NUMBER OF SEQ ID NOS: 31

<210> SEQ ID NO: 1
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 1

Ala Lys Arg Glu Ser Ala Ala
 1               5

<210> SEQ ID NO: 2
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Glu Lys Arg Ala Ser Ala Ala
 1               5

<210> SEQ ID NO: 3
<211> LENGTH: 7
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 3

Ala Lys Arg Lys Ser Ala Ala
  1               5

<210> SEQ ID NO: 4
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Lys Lys Arg Ala Ser Ala Ala
  1               5

<210> SEQ ID NO: 5
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ala Arg Arg Ala Ser Ala Ala
  1               5

<210> SEQ ID NO: 6
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Ala Lys Arg Ala Ser Ala Ala
  1               5

<210> SEQ ID NO: 7
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Pro Lys Arg Ala Ser Ala Ala
  1               5

<210> SEQ ID NO: 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Lys Lys Arg Lys Ser Ala Ala
  1               5
```

```
<210> SEQ ID NO: 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Lys Lys Arg Lys Ser Gly Leu
  1               5

<210> SEQ ID NO: 10
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Tyr Asn Lys Arg Ser Thr Thr Ile
  1               5

<210> SEQ ID NO: 11
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Val Lys Arg Ile Ser Gly Leu
  1               5

<210> SEQ ID NO: 12
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Ala Pro Lys Arg Gly Ser Gly Lys
  1               5

<210> SEQ ID NO: 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Cys Leu Arg Arg Asp Ser His Lys
  1               5

<210> SEQ ID NO: 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 14

Ala Lys Ala Ala Ser Ala Ala
 1               5

<210> SEQ ID NO: 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Ala Ala Arg Ala Ser Ala Ala
 1               5

<210> SEQ ID NO: 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ala Arg Ala Ala Ser Val Ala
 1               5

<210> SEQ ID NO: 17
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Ala Arg Arg Ala Ser Val Ala
 1               5

<210> SEQ ID NO: 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Pro Lys Lys Arg Lys Ser Leu
 1               5

<210> SEQ ID NO: 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Ala Ala Ala Ala Ser Lys Arg
 1               5

<210> SEQ ID NO: 20
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Arg Lys Lys Lys Ser Ala Ala
  1               5

<210> SEQ ID NO: 21
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Ala Lys Lys Ala Ser Ala Ala
  1               5

<210> SEQ ID NO: 22
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Ala Ala Lys Lys Ser Ala Ala
  1               5

<210> SEQ ID NO: 23
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Ala Ala Lys Arg Ser Ala Ala
  1               5

<210> SEQ ID NO: 24
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ala Arg Lys Ala Ser Ala Ala
  1               5

<210> SEQ ID NO: 25
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Lys Lys Ala Ala Ser Ala Ala
```

1               5

<210> SEQ ID NO: 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Ala Lys Arg Ala Ser Glu Ala
        1               5

<210> SEQ ID NO: 27
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Ala Lys Arg Pro Ser Ala Ala
        1               5

<210> SEQ ID NO: 28
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Ala Lys Arg Ala Ser Pro Ala
        1               5

<210> SEQ ID NO: 29
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Ala Lys Arg Gly Ser Ala Ala
        1               5

<210> SEQ ID NO: 30
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Ala Lys Arg Ala Ser Gly Ala
        1               5

<210> SEQ ID NO: 31
<211> LENGTH: 8
<212> TYPE: PRT
<213> ORGANISM: Artificial Sequence
<220> FEATURE:
<223> OTHER INFORMATION: Description of Artificial Sequence: Synthetic -continued

```
    Peptide

<400> SEQUENCE: 31

Arg Arg Arg Arg Ser Ser Ser Arg
  1               5
```